(12) United States Patent
Takei et al.

(10) Patent No.: US 6,602,238 B2
(45) Date of Patent: Aug. 5, 2003

(54) ABSORBENT ARTICLE

(75) Inventors: Shinobu Takei, Haga-gun (JP); Kenji Ando, Haga-gun (JP); Ken Nemoto, Haga-gun (JP)

(73) Assignee: Kao Corporation, Tokyo (JP)

( * ) Notice: Subject to any disclaimer, the term of this patent is extended or adjusted under 35 U.S.C. 154(b) by 127 days.

(21) Appl. No.: 09/854,755

(22) Filed: May 15, 2001

(65) Prior Publication Data

US 2002/0007172 A1 Jan. 17, 2002

(30) Foreign Application Priority Data

May 15, 2000 (JP) ........................................ 2000-141948
Jun. 6, 2000 (JP) ........................................ 2000-169187
Mar. 30, 2001 (JP) ........................................ 2001-102326

(51) Int. Cl.[7] .............................................. A61F 13/15
(52) U.S. Cl. ............................ 604/385.26; 604/385.03; 604/385.22; 604/385.29; 604/385.3; 604/385.01; 604/385.26; 604/385.27; 604/365; 604/324
(58) Field of Search ...................... 604/385.26, 385.27, 604/365, 385.01, 385.24, 370, 373, 372

(56) References Cited

U.S. PATENT DOCUMENTS 5,817,087 A 10/1998 Takabyashi et al.

FOREIGN PATENT DOCUMENTS

| EP | 0 048 011 A1 | 3/1982 |
| EP | 0 626 161 A1 | 11/1994 |
| JP | 5777304 | 5/1982 |
| JP | 57117602 | 7/1982 |
| TW | 342326 | 10/1998 |
| WO | WO 87/04117 | 7/1987 |

*Primary Examiner*—A. Vanatta
*Assistant Examiner*—Angela J Grayson
(74) *Attorney, Agent, or Firm*—Birch, Stewart, Kolasch & Birch, LLP (57) ABSTRACT

A shorts-type absorbent article having leg region forming members 71, 71 arranged in an elongated state at a pair of leg regions 70 arranged around a wearer's leg, wherein each of the leg region elastic members comprises a first and a second elastic member 71a, 71b and the first and second elastic members do not exhibit elastic expansible/contractible property at least at a central area of the portion where the absorbent core exists, and the predetermined parts of the first and second elastic members are fixed to the component of the absorbent article by a second fixing means S, S.

15 Claims, 6 Drawing Sheets

ABSORBENT ARTICLE

BACKGROUND OF THE INVENTION

The present invention relates to an absorbent article such as a disposable diaper offering nice fit, and comfort while worn and enhanced leakage preventive property.

1. Field of the Invention

There has heretofore been known a disposable diaper in which a leg region elastic member for forming leg gathers is disposed across an under-crotch region from one of the two leg regions, which are disposed around wearer's legs, to the other one, and the leg region elastic member is cut off at the under-crotch region.

2. Description of Background Art

In such a disposable diaper, a thready rubber is used as the leg region elastic member, which is small in elongation stress, excellent in adhesive property with respect to a sheet material such as a nonwoven fabric for sandwichingly holding the thready rubber. The reason why such a material is used as the leg region elastic member is as follows. If an elastic member having a large elongation stress such as a thick thread-like rubber or an elastic member with a talc stuck to its outer surface and therefore having a poor adhesive property such as a natural rubber should be used as a leg region elastic member, so-called "rubber removal" would occur, wherein the cutting-off of the leg region elastic member at the under-crotch region causes spread of a released condition of the elongated state of the elastic member over to the side edges of the leg region during the time of manufacture or during the time of wearing such a disposable diaper. As a result, there is such a fear that the fitness around the leg is deteriorated to thereby allow generation of leakage.

However, if an elastic member having a small elongation stress should be used as a leg region elastic member, leakage of urine and feces might occur because its tightening strength around the leg region is insufficient and so the elastic member cannot follow the active motion of the wearer. If an elastic member having a small elongation stress should be arranged at a high elongation ratio in order to solve such a problem as just mentioned, the adhesive property with respect to a sheet such as a nonwoven fabric for sandwichingly holding the elastic member would be lowered.

If the adhesive agent for fixing the elastic member should be increased in quantity in order to prevent the occurrence of rubber removal, flexibility would be lowered due to the increased quantity of adhesive agent and the elongation physical property of the elastic member would be deteriorated to lower the fitness and moreover, physical irritation to the wearer's skin would be resulted. In addition, the adhesive agent would be oozed out from the sheet such as a nonwoven fabric for sandwichingly holding the elastic member. Consequently, the wearer may have an unpleasant feel because of stickiness and diaper rash may be resulted.

Japanese Patent Application Laid-Open Publication Nos. S57-77304 and S57-117602 disclose absorbent articles in which a leg region elastic member is cut off at an under-crotch region. However, those publications do not teach at all a method for obtaining a proper tightening strength around the leg while preventing the occurrence of rubber removal caused by the cutting-off of the leg region elastic member at the under-crotch region.

It is an object of the present invention to provide an absorbent article such as a disposable diaper, in which an elongation stress of an elastic member for forming leg gathers and an arrangement elongation ratio thereof can be determined relatively freely during the time for development of products so that a proper tightening strength around the leg can be obtained and in which fitness and absorption performance can be improved without accompanying with any inconvenience such as deterioration in flexibility around the leg, irritation to the wearer's skin or the like, and a method for manufacturing a laminated sheet capable of efficiently manufacturing a laminated sheet suited to be used for manufacturing such an absorbent article.

Another object of the present invention is to provide an absorbent article, in which so-called rubber removal does not occur at the time of manufacture and at the time of wearing such an absorbent article, in which excellent fitness and absorption performance can be obtained, and in which a concave pocket structure is surely formed in the under-crotch region to thereby enable to obtain an excellent anti-leakage property.

SUMMARY OF THE INVENTION

The present invention has achieved the above objects by providing an absorbent article comprising a liquid-permeable topsheet, a liquid-impermeable anti-leakage sheet and a liquid-retentive absorbent core interposed between the topsheet and the anti-leakage sheet, a leg region elastic member for forming leg gathers being arranged in an elongated state thereof at a leg region arranged around a wearer's leg, wherein the leg region elastic member comprises a first and a second elastic member, and the first and second elastic members each include a pair of gather forming parts arranged at a pair of the leg regions and a traversing part arranged in such a manner as to traverse the absorbent core, gather forming parts of the first and second elastic members at each leg region being arranged such that the gather forming parts are oriented in opposite directions with each other, the gather forming parts of the first and second elastic members are fixed to a component of the absorbent article by a first fixing means, and the first and/or second elastic members do not exhibit elastic expansible/contractible property at least at a widthwise central area of that part of the traversing part where the absorbent core exists, and a predetermined part of the first and/or second elastic member including a portion which does not exhibit elastic expansible/contractible property is fixed to the component of the absorbent article by a second fixing means (the expression "the first invention" used hereinafter refers to this invention).

Moreover, the present invention has achieved the above objects by providing a shorts-type absorbent article comprising a liquid-permeable topsheet, a liquid-impermeable anti-leakage sheet and a liquid-retentive absorbent core interposed between the topsheet and the anti-leakage sheet, a leg region elastic member for forming leg gathers arranged in an elongated state at a leg region arranged around a wearer's leg, wherein the leg region elastic member comprises a first and a second elastic member, and the first and second elastic members each include a pair of gather forming parts arranged at a pair of the leg regions and an extension part extending from the gather forming parts towards a widthwise central area of the absorbent article, the gather forming parts of the first and second elastic members are fixed to a component of the absorbent article by a first fixing means, the extension part of the first and/or second elastic member is fixed to the component of the absorbent article by a second fixing means at a part where the absorbent core exists, and at least a portion of the extension part located at the part where the absorbent core exists exhibits elastic expansible/contractible property, and the first and second elastic members do not exhibit elastic expansible/contractible property at least at a widthwise central area of the part where the absorbent core exists (the expression "the second invention used hereinafter refers to this invention).

Moreover, the present invention has achieved the above objects by providing a method for manufacturing a partly elasticized laminated sheet comprising the steps of applying an adhesive agent as first fixing means to at least one of two consecutive sheets which are stuck to each other in a predetermined pattern, sticking the two consecutive sheets together after the elastic member is introduced while oscillating the elastic member in a direction orthogonal to a flowing direction of the two consecutive sheets so that the elastic member is fixed between the two consecutive sheets through the adhesive agent, dividing the elastic member at a predetermined part, and fixing the predetermined part of the elastic member to at least one of the two consecutive sheets by second fixing means before or after, or at the same time the elastic member is divided (the expression "the third invention" used hereinafter refers to this invention).

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be more particularly described with reference to the accompanying drawings, in which.

DETAILED DESCRIPTION OF THE PREFERRED EMBODIMENTS

Figure 1:
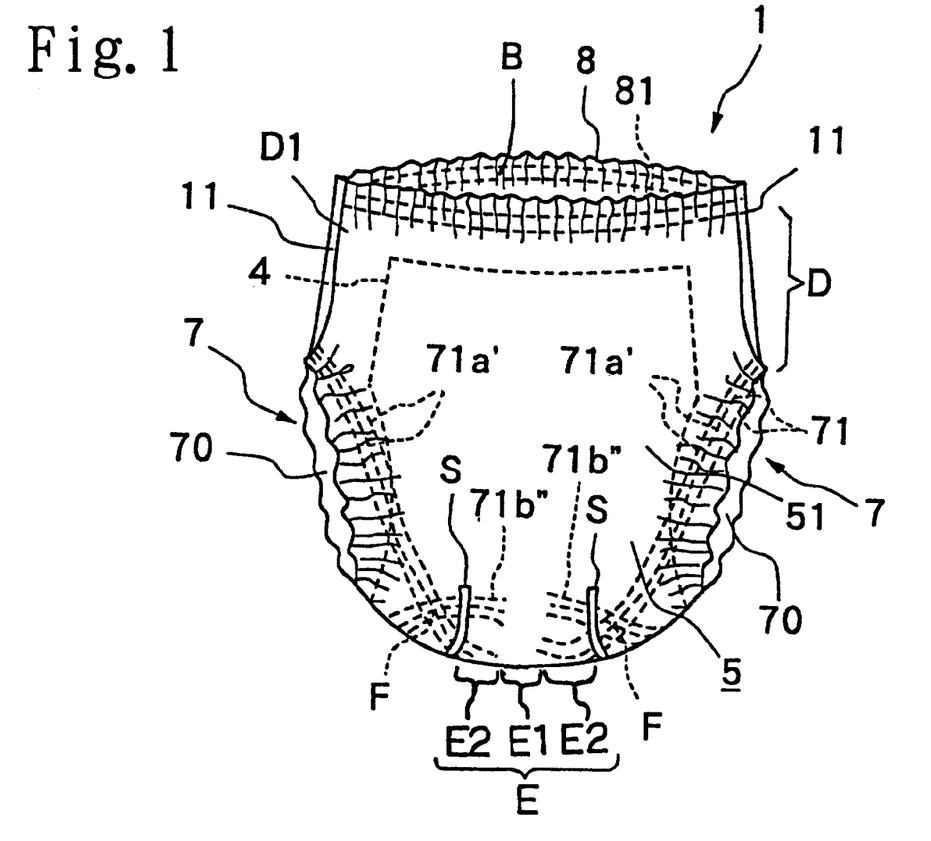
FIG. 1 is a perspective view showing a disposable diaper according to a first embodiment of the present invention.
Figure 2:
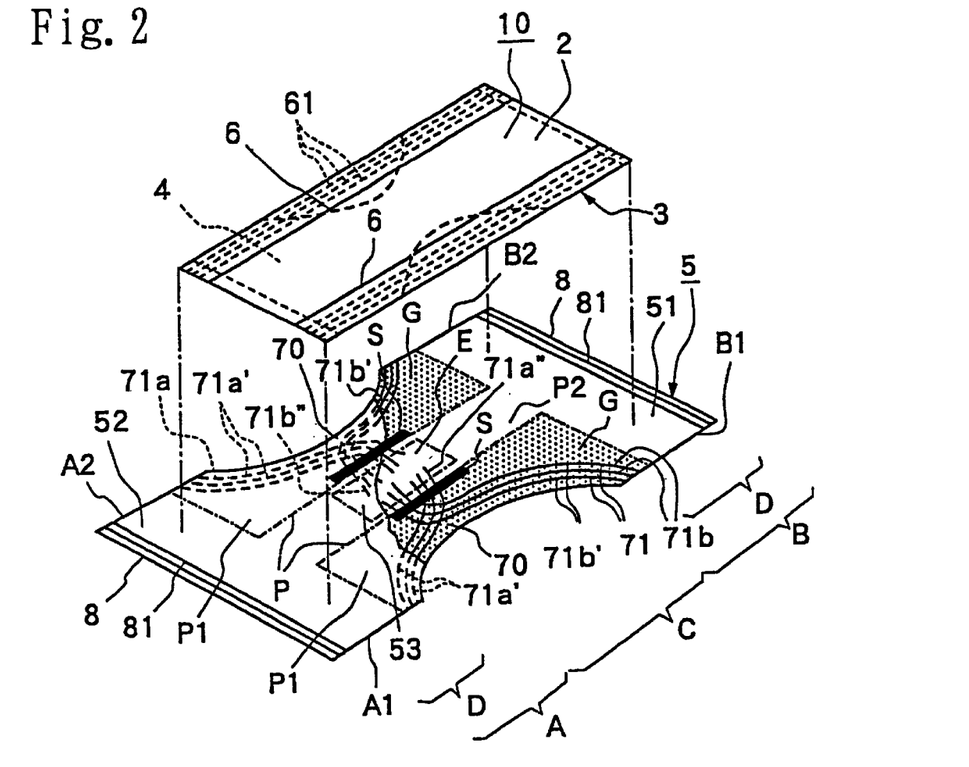
FIG. 2 is an exploded perspective view showing a developed condition of the disposable diaper of FIG. 1.
Figures 3A, 3B, 3C:
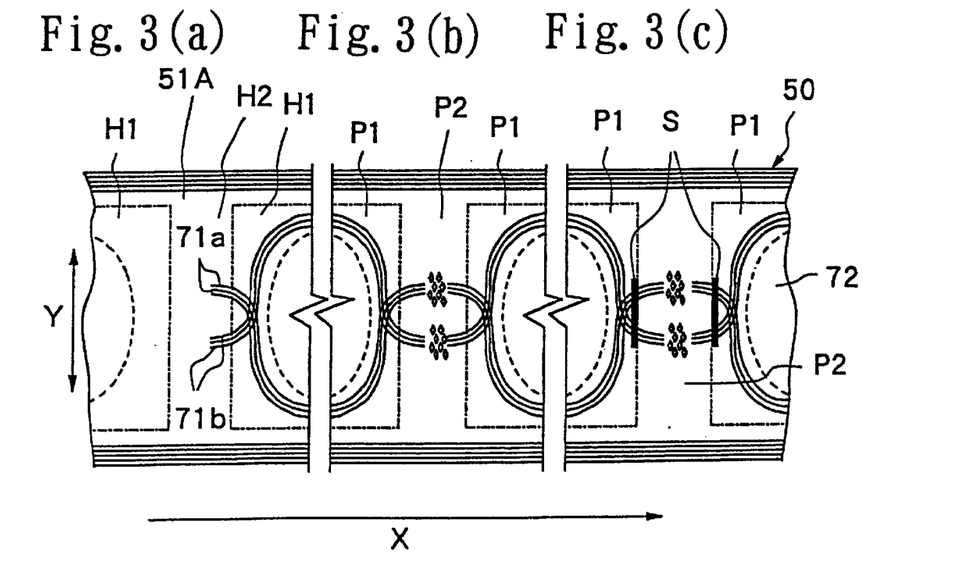
FIG. 3(a), FIG. 3(b) and FIG. 3(c) are views showing the outline of the manufacturing steps employed in a method for manufacturing a laminated sheet according to the present invention.

The present invention will be described hereinafter in the form of preferred embodiments of the present invention. A disposable diaper 1 as a first embodiment of an absorbent article of the present invention is a shorts-type disposable diaper. This shorts-type disposable diaper comprises, as shown in FIGS. 1 to 3, a liquid-permeable topsheet 2, a liquid-impermeable anti-leakage sheet 3 and a liquid-retentive absorbent core 4 interposed between the topsheet 2 and the anti-leakage sheet 3. Elastic members 71 for forming leg gathers are arranged in their elongated states at each of one pair of leg regions 70, 70 arranged around a wearer's leg.

The disposable diaper 1 comprises an absorptive main body 10 comprising the topsheet 2, the anti-leakage sheet 3 and the absorbent core 4, and an outer layer body 5 located outside the absorptive main body 10. This outer layer body 5 is adapted to fixedly join the absorptive main body 10. The disposable diaper 1 includes a stomach-side region A arranged on the wearer's stomach-side, a back-side region B arranged on the wearer's back side, and an under-crotch region C located therebetween. Opposite side edges A1, A2 of the stomach-side region A and opposite side edges B1, B2 of the back-side region B are joined with each other by known joining means such as heat sealing, high frequency sealing, ultrasonic sealing, or the like, to thereby form one pair of leg opening regions 7 and a waist opening region 8.

The topsheet 2, the anti-leakage sheet 3 and the absorbent core 4 are integrated to form the absorptive main body 10 having a vertically elongated rectangular configuration. The absorbent core 4 has an hourglass configuration which is twisted at its central area in the longitudinal direction. The absorbent core 4 is fixedly sandwiched between the topsheet 2 and the anti-leakage sheet 3. The absorptive main body 10 is joined with a widthwise central area of the outer layer body 5 by known joining means with its longitudinal direction in alignment with the longitudinal direction of the disposable diaper, i.e., direction of connection of the stomach-side region A with the back-side region B in an elongated state of the diaper 1. A three dimensional guard 6 is formed on each of the left and right opposite side regions in the longitudinal direction of the absorptive main body 10. Each three-dimensional guard 6 has a free end on the widthwise inner side of the absorptive main body 10 and a fixed end on the outer side. A plurality of three-dimensional guard elastic members 61 are expansibly and contractibly fixed to each three-dimensional guard 6. Owing to those elastic members 61, the three-dimensional guard 6 is erected to prohibit the flow-out of liquid in the widthwise direction of the absorptive main body 10. The plurality of three-dimensional guard elastic members 61 are arranged at predetermined intervals along the longitudinal direction of the absorptive main body 10.

Waist elastic members 81 for forming waist gathers are arranged in their elongated state on the waist opening region 8 along an opening edge part thereof. Specifically, the outer layer body 5 is provided at front and rear end parts thereof with a plurality of waist region elastic members 81 arranged in the widthwise direction over an entire length thereof along the respective end edges. Owing to those waist elastic members 81, annular waist gathers, which are substantially consecutive over the entire circumference, are formed at the waist opening regions 8. Although not shown, a plurality of girth region elastic members are arranged at a girth region D which is located in a lower position than the position where the waist elastic members 81 are arranged at the stomach-side region A and the back-side region B but in a higher position than the under-crotch region C (that is to say, upper side than the leg opening parts 7, 7), over the widthwise direction of the outer layer body 5.

In the disposable diaper 1 according to this embodiment, the leg region elastic member 71 for forming the leg gathers is arranged in its elongated state thereof at a leg region 70 arranged around the wearer's leg.

The leg region elastic member 71 comprises a first and a second elastic member 71a, 71b. Each of the first and second elastic members 71a, 71b includes, respectively, one pair of gather forming parts 71a', 71a', 71b', 71b' which are arranged at the pair of leg regions 70 and traverse part 71a", 71b" arranged in such a manner as to traverse the absorbent core 4 at a central area of the under-crotch region C. The gather forming parts of the first and second elastic members 71a, 71b are arranged along opposite side edges of the under-crotch region C which are in the form of recess. Each traverse part 71a", 71b" is located between the pair of gather forming parts of each elastic member and continuous with the gather forming part on each side.

Each traverse part 71a", 71b" is divided into one pair of extension parts 71a", 71b" extending from each gather forming part towards the widthwise central area of the diaper 1.

The extension parts 71a", 71b" in the first and second elastic members 71a, 71b are curved in an opposite direction to the curving direction of the gather forming parts and extended in a direction away from the side edge of the under-crotch region C.

The gather forming parts 71a', 71b' of the first and second elastic members in each leg region 70 are arranged in such a manner as to be oriented in opposite directions to each other. More specifically, in each leg region 70, the gather forming part 71a' of the first elastic member is arranged in such a manner as to be oriented towards the stomach-side region A from the under-crotch region C, while the gather forming part 71b' of the second elastic member is arranged in such a manner as to be oriented towards the back-side region B from the under-crotch region C.

The gather forming parts located on both sides in the widthwise direction of the diaper are arranged in such a manner as to be oriented towards the same side, i.e., towards either the stomach-side region A or the back-side region B. The first and second elastic members 71a, 71b are crossed with each other at the under-crotch region C, thereby forming one pair of crossing parts F, F on left and right sides in the under-crotch region C.

The gather forming parts 71a', 71b' of the first and second elastic members 71a, 71b are fixed in their elongated state to the outer layer body 5 as a component of the disposable diaper 1 by an adhesive agent G as the first fixing means. Specifically, the first and second elastic members 71a, 71b are arranged between two sheet materials 51, 52 which constitute the outer layer body 5, and the gather forming parts 71a', 71b' are adhesively fixed to either one or both of the sheet materials 51, 52 through the adhesive agent G.

One ends of the first and second elastic members 71a, 71b are located at one side edge parts of the stomach-side region A and the back-side region B. In a state wherein opposite side edges A1, A2 of the stomach-side region A and opposite side edges B1, B2 of the back-side region B of the diaper 1 are joined with each other, end parts of the first and second elastic members 71a, 71b are overlapped with each other and as shown in FIG. 1, substantially consecutive annular leg gathers are formed on peripheral edge parts of the leg opening parts 7, 7 of the diaper 1 over the entire circumference thereof.

The first and second elastic members 71a, 71b do not exhibit their elastic expansible/contractible property at the parts where the absorbent core 4 exists. That is to say, the first and second elastic members 71a, 71b are cut off at the traverse parts 71a", 71b" (more specifically, between the extension parts), respectively, and an area E where the first and second elastic members 71a, 71b do not exhibit expansible/contractible property is formed at the areas where the absorbent core 4 exists. Predetermined parts of the first and second elastic members 71a, 71b are fixed to the outer layer body 5 as a component of the diaper 1 by heat sealing as a second fixing means. More specifically, the first elastic members 71a is divided into left and right sides of the diaper 1 are formed from a single consecutive elastic member which is introduced in the elongated state to a manufacturing line of diapers and then, cut off so as to be divided into a left and a right part at the central area of the part where the absorbent core 4 is disposed. The same is also applicable to the second elastic members 71b. Those portions of the first and second elastic members 71a, 71b which are each introduced as a single elastic member and then, fixed by the first and second fixing means exhibit the expansible/contractible property without being released their elongated state by the cut-off. However, those portions which are not fixed by any of the first and second fixing means are released their elongated state by the cut-off and become unable to exhibit the expansible/contractible property. The area E where the first and second elastic members do not exhibit their elastic expansible/contractible property is formed at the part where the absorbent core 4 exists. In the diaper 1 of this embodiment, the area E1 of a predetermined width where the first and second elastic members 71a, 71b do not exist is formed at the widthwise central area of that part where the absorbent core exists 4. Moreover, an area E2 where the first and second elastic members 71a, 71b exist but they do not exhibit the elastic expansible/contractible property is formed on each side of the area E1. Predetermined parts of the first and second elastic members 71a, 71b are fixed to the outer layer body 5 as a component of the diaper 1 by heat sealing. The expression "do not exhibit the expansible/contractible property" refers to not only a state wherein elastic members are provided but the elongated state of the elastic members is released or elasticity of the elastic members is lost by heating or other means, but also a state wherein no elastic member exists at that portion. The expression reading as the elastic members are "divided" used herein refers to a state wherein those portions of the elastic members which exhibit the elastic expansible/contractible property are divided through those portions of the elastic members where such elastic expansible/contractible property is not exhibited. It is preferred that elastic members are divided by cutting-off of elastic members.

Figure 4:
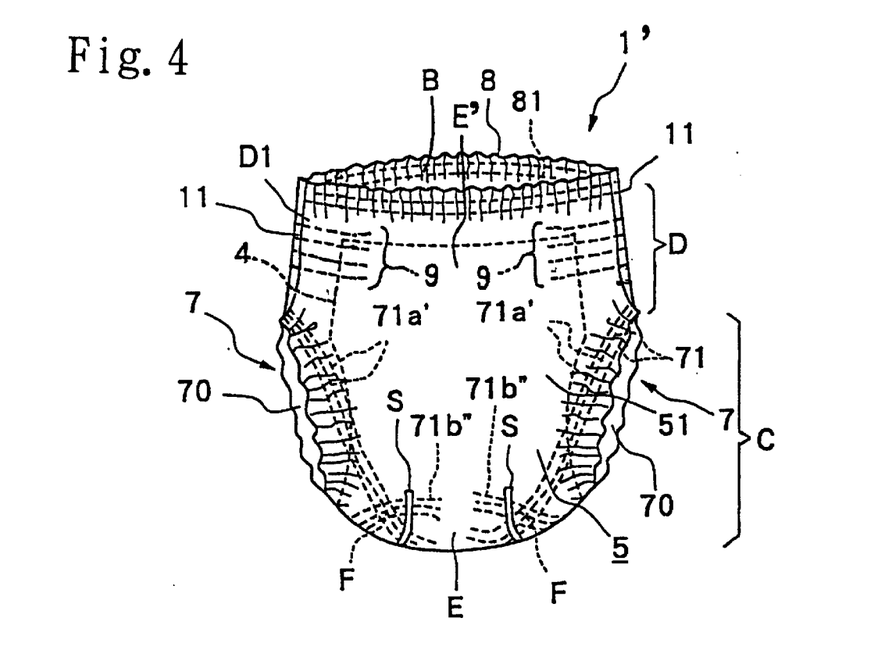
FIG. 4 is a perspective view showing a disposable diaper according to a third embodiment of the present invention.

FIGS. 1 and 4 are schematic views. In those Figures, although the width of the absorbent core at the under-crotch region C is larger than the width between the parts S, S where a heat seal is applied (the width of the area E where no elastic expansible/contractible property is exhibited), the width of the absorbent core at the under-crotch region C is actually generally same as the width between S and S.

More specifically, the traverse parts 71a", 71b" of the first and second elastic members 71a, 71b include a portion which is not fixed to the outer layer body 5 at a part overlapped with the absorbent core 4, i.e., part where the absorbent core 4 exists. The first and second elastic members 71a, 71b are each cut off at the portion which is not fixed to the outer layer body 5. The first and second elastic members 71a, 71b are fixed at opposite sides of the cut-off area in the traverse part to the second fixing means. FIGS. 1 and 2 indicate those places by reference character S where a heat seal is applied as the second fixing means. As illustrated, in this embodiment, an adhesion area P1 and a non-adhesion area P2 are formed. In the adhesion area P1, two sheets 51, 52, which are arranged at opposite sides in such a manner as to sandwich the first and second elastic members 71a, 71b, are fixed by the first fixing means, while in the non-adhesion area P2, the two sheets 51, 52 are not fixed by the first fixing means. The heat seal as the second fixing means is formed at area in the vicinity of a border line between the adhesion area P1 and the non-adhesion area P2, more specifically at the adhesion area P1 adjacent to the border line (indicated by one dot chain line of FIG. 2). The first and second elastic members 71a, 71b are fixed at an area located more inside in a widthwise direction than the pair of crossing parts F, F which are formed at opposite left and right sides of the under-crotch region C.

In this embodiment, the first and second elastic members 71a, 71b are arranged between the two sheet materials 51, 52 which constitute the outer layer body 5. Fixture by heat sealing as the second fixing means is achieved by fixingly sandwiching the elastic members between the two sheet materials which are welded together, or by welding the elastic members themselves to either one or both of the sheet materials.

The first fixing means in the first invention is a means for fixing the gather forming part of the leg region elastic member to a component, preferably the sheet material, of the absorbent article. As the first fixing means, adhesive agent, heat sealing, ultrasonic sealing, etc. can be listed. Among them, adhesive agent is preferable as in this embodiment. As the adhesive agent as the first fixing means, various kinds of known adhesive agent can be used. Among them, hot melt adhesive agent is preferable, and particularly preferable is SEBS [styrene-(ethyrene-co-butyrene)-styrene block copoymer], SBS (styrene-butadiene-styrene block copolymer), SIS (styrene-isoprene-styrene block copolymer), or the like.

The second fixing means is a means for fixing a predetermined part of the leg region elastic member to a component of the absorbent article. This means is different from the first fixing means. Otherwise, it may be same as the first fixing means but in which the process is executed in such a manner as to obtain a different joining strength (strong joining strength) or in which the means is executed in a different process from the process for treating the first fixing means (preferably, process which is executed after the process for the first fixing means is executed). As the second fixing means, heat sealing, ultrasonic sealing or adhesive agent is preferable. Among them, adhesive agent is particularly preferable.

As one example wherein the first fixing means is different from the second fixing mean, there can be listed a case wherein the first fixing means is adhesive agent and the second fixing means is heat and/or pressure treatment such as heat sealing and ultrasonic sealing. As one example wherein the first fixing means is same as the second fixing means but in which the means is executed in such a manner as to obtain a larger joining strength than the first fixing means, there can be listed a case wherein the first and second fixing means are adhesive agent but (a) the basis weight of the applying adhesive agent (quantity of the applying adhesive agent per unit area) as the second fixing means is larger than the basis weight of the applying adhesive agent of the first fixing means, (b) the adhesive agent as the second fixing means is applied on the top of the adhesive agent as the first fixing means in an overlapping manner, (c) the adhesive agent is different in kind or composition, (d) the applying pattern of the second fixing means is different from the applying pattern of the first fixing means, and (e) a combination of two or more of the above items (a) to (d).

The outer layer body 5 in the disposable diaper 1 of this embodiment comprises one pair of sheet materials, i.e., the outer layer sheet 5 forming the outer surface of the disposable diaper and the inner layer sheet 52 laminated and adhered to the inner side of the outer layer sheet 51, and the various elastic members, i.e., the leg region elastic member 71, the waist region elastic member 81 and the girth region elastic member (not shown), which are fixingly sandwiched between the two sheets 51, 52. Since the outer layer body 5 can be manufactured without removing the elastic member (s) at the under-crotch region of the diaper, high speed of the manufacturing line can be realized.

This outer layer body 5 can be manufactured easily and efficiently by a below-described method as a first embodiment of a method for manufacturing a laminated sheet of the present invention. In a manufacturing method of the first embodiment, first, of a continuous sheet 51A of the outer layer sheet and a continuous sheet (not shown) of the inner layer sheet 52 stuck to each other, at least one continuous sheet 51A is, as shown in FIG. 3(a), applied with adhesive agent as the first fixing means in a predetermined pattern (applying process). In this embodiment, the adhesive agent is intermittently applied at predetermined intervals in a flowing direction X of the two continuous sheets (only one is shown). By this, adhesive applied parts H1 and adhesive non-applied parts H2 are alternately formed on the continuous sheet in the flowing direction X of the continuous sheet. The application pattern of the adhesive agent in this applying process is not particularly limited, but it can be in the form of stripe, spiral, solid, dots, or the like. The two continuous sheets are consecutively conveyed in the same direction. The intermittent application of the adhesive agent may be performed partially.

Then, in order to intermittently fixing the first and second elastic members 71a, 71b between the two continuous sheets through adhesive agent, the first and second elastic members 71a, 71b are introduced in their elongated state while being oscillated in a direction Y orthogonal to the flowing direction X of the sheets and then, the sheets are stuck to each other (introducing and sticking process). In this embodiment, although the continuous sheet of the inner layer sheet 52 is stuck immediately after the first and second elastic members 71a, 71b, illustration of the continuous sheet of the inner layer sheet is omitted. In this introducing and sticking process, the two continuous sheets are stuck to each other at the adhesive applied parts H1 to thereby form the adhesion area P1, and the non-adhesion area P2 where the two continuous sheets are not stuck to each other is also formed. The first and second elastic members 71a, 71b are fixed between the two continuous sheets at the adhesion area P1 but they are not fixed between the two continuous sheets at the non-adhesion area P2.

Subsequently, as shown in FIG. 3(b), the first and second elastic members 71a, 71b are cut off at the part P2 where they are not fixed to the two continuous sheets (cutting off process). Moreover, as shown in FIG. 3(c), the elastic members 71a, 71b thus cut off are partly fixed to the two continuous sheets by heat sealing as the second fixing means (fixing process). That portion indicated by S of FIG. 3(c), is the place where heat sealing is applied.

Via the processes as just mentioned above, a partially elasticized laminated sheet 50 can be obtained. The outer layer body 5 can be obtained by cutting off and removing an extra part 72 for forming a leg region from the laminated sheet 50 and cutting off the laminated sheet 50 into individual outer layer bodies 5. In this embodiment, the elastic members only excluding the leg region elastic member are introduced into the introducing and sticking process.

In the first to third inventions, the material for forming the two sheet materials in the case where the elastic members 71a, 71b are fixed between the two sheet materials is preferably one which contains heat fusing fibers together with the two sheets. Particularly preferably, examples of such material include a nonwoven fabric containing core-sheath type adhesive composite fibers (for example, composite fibers of a PET core and a PE sheath), a nonwoven fabric containing a side-by-side type adhesive composite fibers and a bicomponent nonwoven fabric containing both high melting point and low melting point synthetic fibers, because a high fixing strength can be obtained owing to high heat sealing property. The materials for forming the two sheet materials may be same or different.

In the case where heat sealing is used as the second fixing means, the sealing area may be sealed (solid seal) over its entire surface. However, from the view point for preventing the sealing area from becoming hard and the feeling from becoming bad, sealing is preferably partly made in a predetermined pattern (dots pattern or the like). The heat sealing is usually performed by inserting the leg region elastic member together with a seat material for fixing the leg region elastic member between one pair of seal rolls. The pair of seat rolls are preferably a pattern roll and a backup roll. Only one of the rolls may be a heat roll or both of the rolls may be heat rolls. Moreover, it is desirable to use a cylinder having a bore diameter of less than 200 mm as the pattern roll and/or the backup roll and to use a pressure means for applying a pressure of 5 to 50 kgf/cm2. By doing so, material can be machined under optimal conditions and machining conditions can be stabilized. It is desirable that no damage such as breakage is given to the sheet material, etc. for fixing the leg region elastic member at the time of heat sealing.

In the case where the elastic members 71a, 71b are each composed a plurality of elastic members, it is preferred that a plurality of elastic members are spacedly arranged at those parts where the second fixing means is applied. The reason is that the feeling of the laminated sheet 50 can be prevented from degrading by forming the elastic members into a bundle to increase the thickness and the elastic members can surely be fixed by sealing the opposite ends of the individual elastic members.

For cutting off the elastic members 71a, 71b, various kinds of known cutting means can be used. For example, a pinch cutter, a rotary die cutter, a heat seal cutter, an ultrasonic cutter, a water jet cutter, and the like can be used. In particular, in the case of elastic members composed of natural rubber, spandex, or the like, a pinch cutter, a rotary die cutter, a heat seal cutter, or the like is preferably used because of a reduced load of facilities.

The manner of cutting off the elastic members 71a, 71b is not limited. For example, the elastic members may be cut off either individually or in the form of a bundle of plural elastic members. In the former case, the elastic members can surely be cut off by limiting the objects to be cut, while in the latter case, damage of the sheet material caused by cut-off can be reduced to the least possible level.

The disposable diaper 1 of the first embodiment can easily be manufactured by fixedly joining an absorptive main body 10 manufactured in accordance with a normal method with the outer layer body 5 obtained in the manner as described above by a joining means known per se and then joining the opposite side edges A1, A2 of the stomach-side region A with the opposite side edges B1, B2 of the back-side region B, respectively.

The material for forming the component members of the disposable diaper 1 of the first embodiment will now be described. As the material for forming the topsheet 2, the anti-leakage sheet 3, the absorbent core 4, the sheet material or elastic surface sheet 2 for forming the three-dimensional guard 6, the waist region elastic member 81 and the girth region elastic member, those which have heretofore been used for a disposable diaper, etc. can be used without any particular limitation. As one example of the absorbent core, there can be listed those which can be obtained by wrapping a fiber material such as a pulp fiber and a water-absorptive polymer with a liquid-permeable wrapping material such as a tissue paper, a nonwoven fabric, or the like.

As the material for forming the elastic members 71a, 71b, various kinds of known elastic materials can be used. As such raw material, expansible/contractible raw material such as, synthetic rubber such as styrene-butadiene, butadiene, isoprene and neoprene, natural rubber, EVA, expansible polyolefine, urethane and the like can widely be used. The elastic members 71a, 71b are preferably in the form of a thread or tape having a configuration in section of rectangle, regular square, circle or polygon. Elastic material having such a property as to be thermally plasticized is also preferably used.

As the material for forming the outer layer sheet 51 and the inner layer sheet 52 which constitute the outer layer body, a flexible sheet is preferably used, which has a liquid-resisting property, a liquid-impermeable moisture-permeable property and an air-permeable property, and which can offer the feel resembling an underwear. Specifically, there can be listed, among others, a woven fabric, a nonwoven fabric, a film, a moisture-permeable film, an aperture film, and a composite material thereof.

The shorts-type disposable diaper of this embodiment can be used in the same manner as the normal shorts-type disposable diaper. In the disposable diaper 1 of this embodiment, the first and second elastic members 71a, 71b are cut off at the part traversing the under-crotch region and the area E where the leg region elastic member 71 exhibits no expansible/contractible property is formed at the part where the absorbent core 4 exists. Accordingly, the absorbent core 4 is hardly shrunk during the time of wearing the diaper. Owing to this feature, a favorable absorptive capability can be maintained even if the width of the absorbent core 4 is reduced. By this, miniaturization of the absorbent core 4, reduction of material to be used, etc. can be realized. Moreover, since the absorbent core is difficult to be gathered, the diaper can easily be put on the wearer and in addition, it can offer a nice-looking plain outer appearance.

From the viewpoint to obtain a disposable diaper capable of offering nice fit and excellent absorptive capability by obtaining a proper tightening force around the leg, the first and/or second elastic member 71a, 71b is preferably a belt-like elastic member (for example, flat rubber having a width of 1 to 7 mm, or the like).

For the same reason, each of the first and second elastic members 71a, 71b preferably has an elongation stress of 30 gf or more in the elongation ratio when they are fixed to the absorbent article. The upper limit is appropriately 200 gf.

In the disposable diaper 1, the first and second elastic members 71a, 71b are fixed to prescribed portions by the second fixing means, so that so-called rubber removal does not occur and excellent fitness and absorption performance can be obtained.

Particularly, even in a case where elastic members having a large expansible/contractible stress such as, for example, flat rubber, or elastic members having a deteriorated adhering ability such as natural rubber whose surface is attached with talc are used, or even in a case where elastic members having a small expansible/contractible stress are arranged at a high rate of elongation, the so-called rubber removal does not occur. Accordingly, in order to obtain a proper tightening force around the leg, the elastic member for forming leg gathers and the rate of arrangement elongation thereof can properly be determined, and the fitness and absorptive capability can be enhanced efficiently and economically. Moreover, in the disposable diaper 1 of this embodiment, since it is unnecessary to increase the quantity of adhesive agent, there is no fear of the occurrence of lowering of flexibility and adverse effect to the wearer's skin caused by the use of large quantity of adhesive agent, uncomfortable feeling due to stickiness, etc.

The "elongation ratio of the elastic member fixed to the absorbent article" and the "elongation stress of the elastic member" are measured as follows:

[Elongation Ratio] In a developed condition of a product, i.e., in a condition spread in a planar manner (see FIG. 3), the elastic member is marked at prescribed intervals (X) and then pealed off from the sheet between which the elastic member is sandwiched. In a thoroughly contracted condition of the pealed-off elastic member per se, the intervals (Y), which have been the marked intervals (X), are measured, and the elongation ratio is obtained by $$[(X/Y)-1] \times 100(\%).$$

[Elongation Stress] A single elastic member is pulled by a tensile tester in a initial length of 50 mm and at a tensile rate of 300 mm/min. The stress when the elastic member reaches at a prescribed elongation ratio is measured.

According to the above-mentioned method for manufacturing a laminated sheet, a partly elasticized laminated sheet, which is preferably used for manufacturing, in particular, an absorbent article such as a disposable diaper, can be manufactured efficiently and economically. Any of the first and second fixing means in the third invention is a means for fixing elastic members between two continuous sheets. The second fixing means refers to a means different from the first fixing means (adhesive agent), or a same means (adhesive agent) as the first fixing means but in which the means is executed in such a manner as to obtain a different joining strength or in which the means is executed in a different process (preferably, process which is executed after the process for the first fixing means is executed). As the second fixing means, there can be listed such physical fixing as heat sealing (including ultrasonic sealing), adhesive agent, press-fit, engagement, and the like. Among them, heat sealing or adhesive agent is preferred.

A method for manufacturing a disposable diaper and a laminated sheet as a second embodiment of a method for manufacturing an absorbent article and a laminated sheet of the present invention will be described hereinafter. A method for manufacturing a disposable diaper and a laminated sheet of a second embodiment is different from the first embodiment only in the respect that the second fixing means is adhesive agent instead of heat sealing. Only those points different from the first embodiment will be described and description on the construction same as the first embodiment is omitted. With respect to those points which are not described in particular, the description made hereinbefore with respect to the first embodiment including preferred embodiments, etc. is applicable where appropriate.

In the case where adhesive agent is used as the second fixing means, adhesive agent may be consecutively applied in a belt-like pattern to the two continuous sheets in the flowing direction Y. However, in view of cost reduction, enhancement of feeling (hardness of the applying part), reduction of oozing-out/deposition of adhesive agent in the production process, and the like, it is preferred that adhesive agent as the second fixing means is applied to the area in the vicinity of the border line P between the adhesion area P1 where the two continuous sheets are adhered to each other by adhesive agent as the first fixing means and the non-adhesion area P2 where the two continuous sheets are not adhered to each other. In the diaper of the second embodiment, adhesive agent as the second fixing means is applied to the same part as the part where heat sealing is applied in the first embodiment.

In order to apply the adhesive agent as the second fixing means to a selected specific part, an applying apparatus and a positioning apparatus may be used. As the applying apparatus, any of a contact-type and a non-contact-type apparatus may be used. As a contact-type apparatus, a slot coater or the like is used, while as a non-contact type apparatus, a spiral splay, a curtain splay, a bead gun, or the like is used. As a positioning apparatus, a gun controller, or the like is used. For use, line speed and trigger signal are input and output thereof is connected to the applying apparatus. By this, adhesive agent can be applied to a desired part.

In the case where both the first and second fixing means are adhesive agent as in this embodiment, the basis weight of the adhesive agent of the second fixing means part (part where the second fixing means is executed) is preferably larger than the basis weight of the adhesive agent of the first fixing means (part where the first fixing means is executed). The kind of adhesive agent to be used may be same or different between the first fixing means and the second fixing means.

According to the method for manufacturing a disposable diaper and a laminated sheet of the second embodiment, the same function and effect as in the method for manufacturing a disposable diaper and a laminated sheet of the first embodiment can be exhibited.

A disposable diaper 1' as a third embodiment of an absorbent article of the present invention will now be described with reference to FIG. 4. Different points from the disposable diaper 1 of the first embodiment will be described hereinafter and description on the same points is omitted. With respect to those points which are not described in particular, the description made hereinbefore with respect to the first embodiment including the preferred forms, is applicable where necessary. In the disposable diaper 1' of the third embodiment, a plurality of girth region elastic members 9 are arranged at predetermined intervals in the widthwise direction of the diaper 1' at the girth region D which is located lower than the position where the waist elastic member 81 is arranged but higher than the under-crotch region C (that is to say, upper side than the leg opening parts 7, 7), respectively, in the stomach-side region A and in the back-side region B. The girth region elastic members 9 do not exhibit expansible/contractible property at the parts where the absorbent core 4 exists. That is to say, the girth region elastic members 9 are divided at the widthwise central area of the diaper 1. An area E' where the girth region elastic members 9 do not exhibit elastic expansible/contractible property is formed at the part where the absorbent core 4 exists. Each girth region elastic member 9 is disposed between the two sheets which constitute the outer layer body 5. The girth region elastic member 9 is fixed to the outer layer body 5 at area in the vicinity of the side joint parts 11, 11 of the diaper 1' but it is not fixed to the outer layer body 5 at the widthwise central area where the absorbent core 4 exists. The girth region elastic member 9 is divided at the part which is not fixed to the outer layer body 5.

According to the disposable diaper 1' of the third embodiment, since the girth region elastic member 9 is arranged at the girth region D, fitness is enhanced at the user's girth region. In addition, wearing awareness and anti-leakage effect are by far excellent. Moreover, since the girth region elastic member 9 does not exhibit the elastic expansible/contractible property at the part where the absorbent core 4 does not exist, the absorbent core 4 is effectively prevented from shrinking and twisting during the time of wearing such a diaper. For this reason, absorptive capability can be maintained even if the width of the absorbent core 4 is reduced. By this, miniaturization of the absorbent core 4, reduction of material to be used, etc. can be realized. Moreover, since the absorbent core is difficult to be gathered, the diaper can easily be put on the wearer and in addition, it can offer a nice-looking plain outer appearance. In the case where the disposable diaper 1' of the third embodiment is used as a disposable diaper for an adult person, an urine blotting pad is often separately inserted between the topsheet 2 and the wearer. In such a case, if no shrinkage nor twisting occurs to the absorbent core, the urine blotting pad can stably be placed in a predetermined position and therefore, leakage caused by displacement of the urine blotting pad can be prevented effectively.

Figure 5:
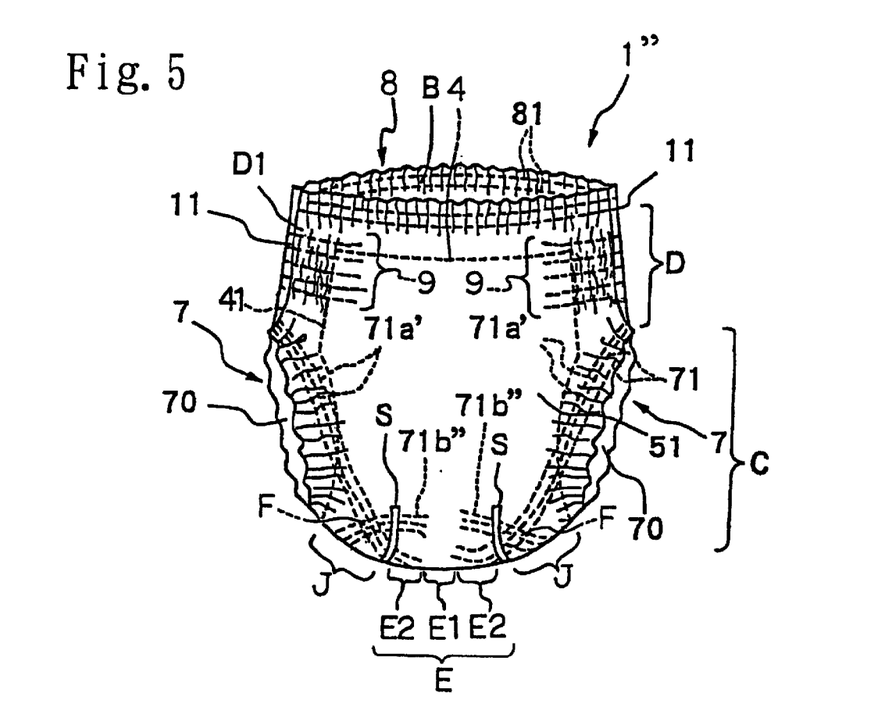
FIG. 5 is a perspective view showing a disposable diaper according to a fourth embodiment of the present invention.
Figure 6:
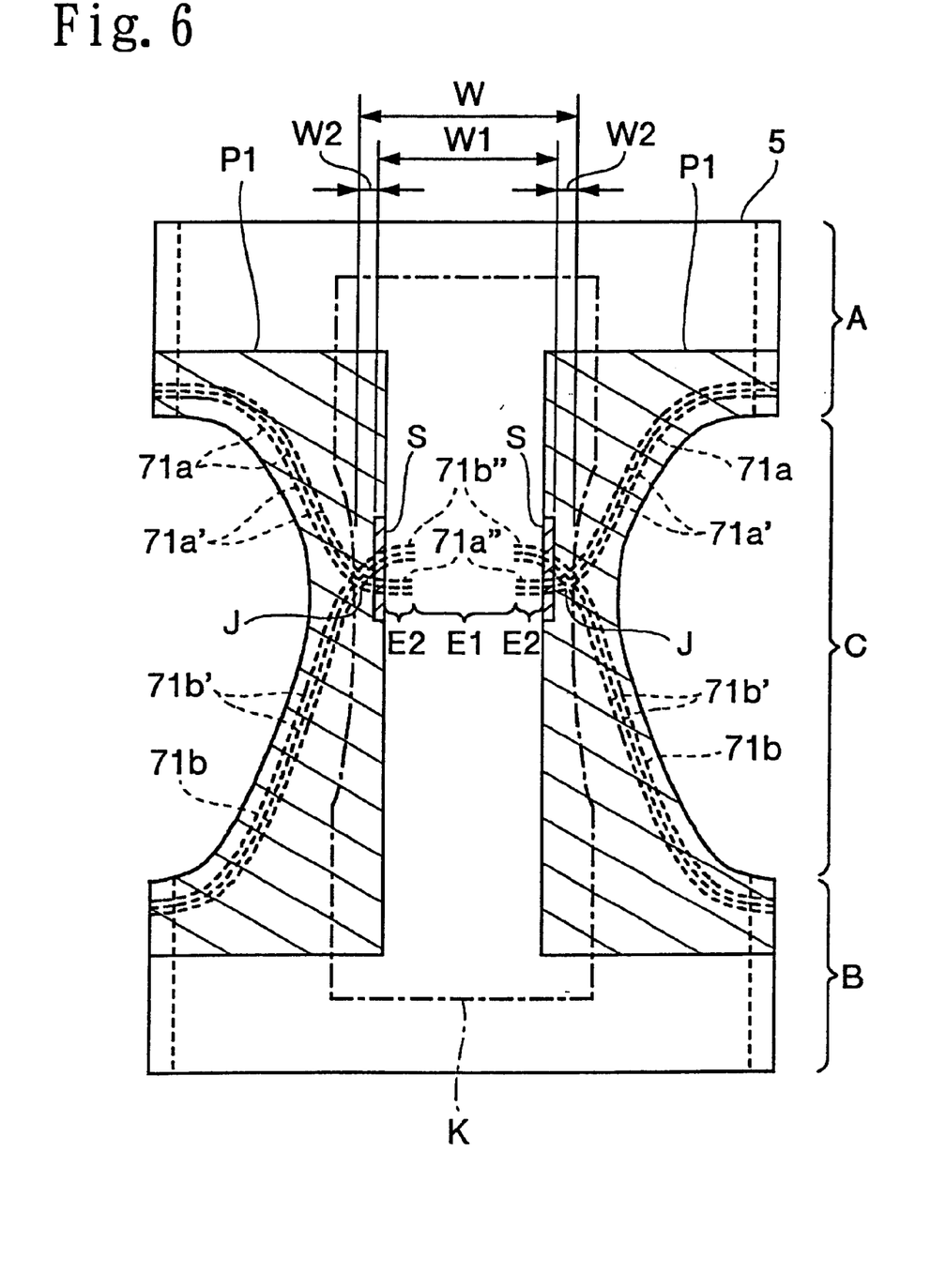
FIG. 6 is a plan view schematically showing the disposable diaper according to the fourth embodiment of the present invention.

A disposable diaper 1" of a fourth embodiment will now be described with reference to FIGS. 5 and 6. Only those points which are different from the disposable diaper 1 of the first embodiment will be mainly described hereinafter and description on the same points is omitted. With respect to those points which are not described in particular, the description made hereinbefore with respect to the first embodiment including preferred embodiments, etc. is applicable where appropriate.

In the disposable diaper 1" of the fourth embodiment, extension parts 71a", 71b" of the first and/or second elastic members are fixed to an outer layer body 5 as a component material of the diaper at a part K where an absorbent core 4 exists by heat sealing as the second fixing means. At least one portions of the extension parts 71a", 71b" located at the part K where the absorbent core exists exhibits the elastic expansible/contractible property. Specifically, a part J, which is located at the part K where the absorbent core 4 exists and which is located more outside in a widthwise direction of the diaper 1 than a part S where heat sealing as the second fixing means is applied, is maintained in its elongated state and exhibits the elastic expansible/contractible property. The width W2+W2 (see FIG. 6) of that portion of the extension part 71a" and/or extension part 71b" where the extension part 71a" and/or extension part 71b" located the part where the absorbent body 4 exists exhibits the elastic expansible/contractible property is 5 to 70% and particularly preferably 5 to 50% with respect to the width W of the absorbent core 4 at that part.

Figure 7:
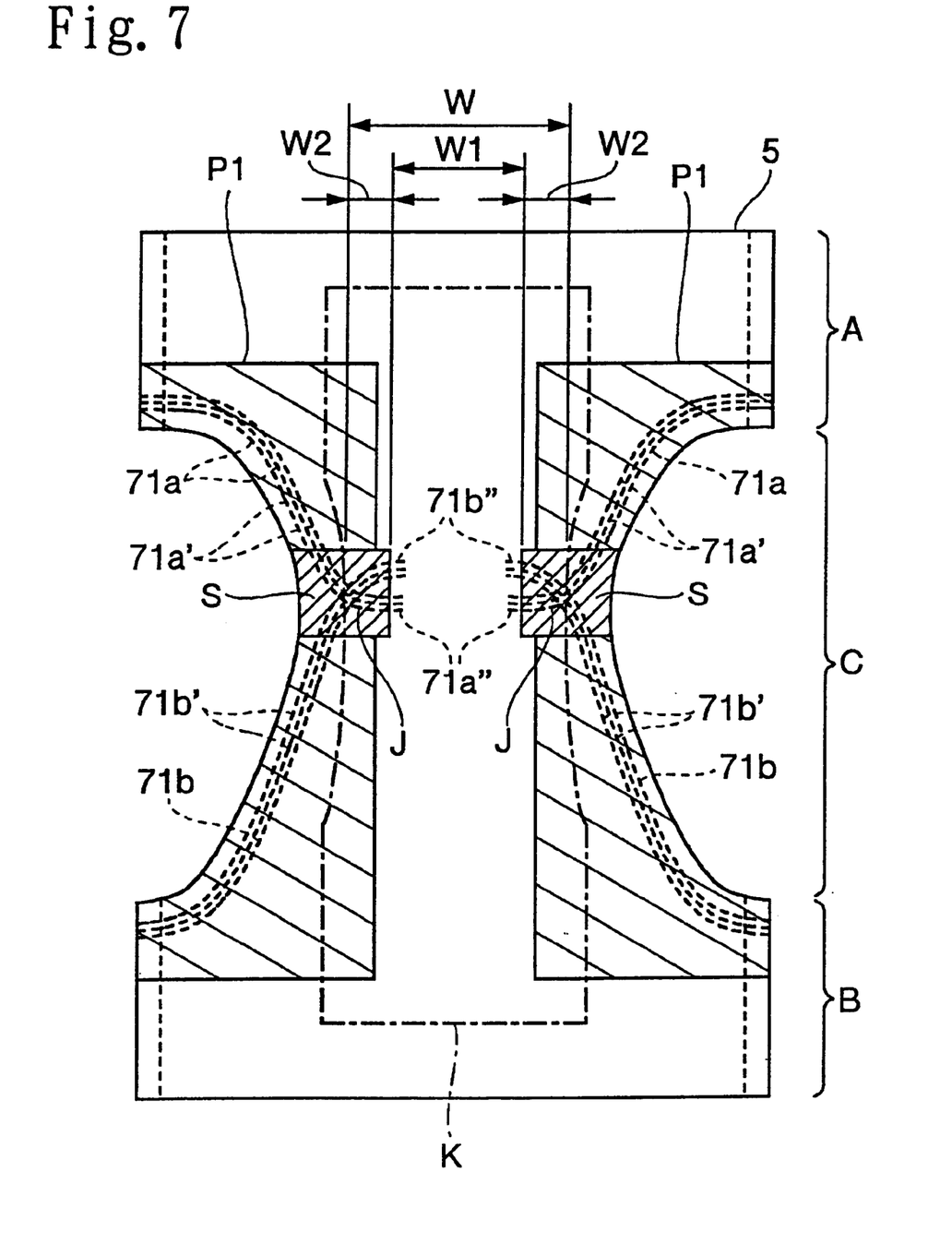
FIG. 7 is a plan view (like FIG. 6) schematically showing an outer layer body of a disposable diaper according to a fifth embodiment of the present invention.

On the other hand, the first and second elastic members 71a, 71b do not exhibit the elastic expansible/contractible property at a widthwise central area of the part K where the absorbent core 4 exists. That is to say, an area E1 where the first and second elastic members 71a, 71b do not exist and an area E2 where the first and second elastic members 71a, 71b exist in their elongation released-state are formed on a part which is located more inside in a widthwise direction of the diaper 1 than the part S where heat sealing as the second fixing means is applied. In those two areas E1, E2, the first and second elastic members 71a, 71b do not exhibit the elastic expansible/contractible property. The width W1 of the area E (E1, E2) (see FIG. 6) where the first and second elastic members 71a, 71b do not exhibit the elastic expansible/contractible property is preferably 30 to 95% and particularly preferably 50 to 95% of the width W of the absorbent core 4 at that part. A hatched part P1 of FIGS. 6 and 7 show an area where adhesive agent G as the first fixing means is applied.

A plurality of girth region elastic members 9 are arranged at predetermined intervals in a widthwise direction of the diaper 1 on opposite left and right sides of the girth region D in both the stomach-side region A and back-side region B, respectively. The expression "girth region D" refers to a portion which is located in a lower side than the position where the waist region elastic member 81 is arranged but in an upper side than the leg opening parts 7, 7 (see FIG. 5). The girth region elastic members 9 are fixedly arranged in their elongated state at least at those parts which are located more outside than the opposite side edges 41, 41 of the absorbent core 4, respectively, such that the elastic expansible/contractible property is exhibited. The girth region elastic members 9 are not arranged at least at a widthwise central area of the part where the absorbent core 4 exists in such a manner that the elastic expansible/contractible property is exhibited. The expression "not arranged . . . in such a manner that the elastic expansible/contractible property is exhibited" refers to the following two states. In the first state, the elastic members are not arranged at that part, while in the second state, the elastic members are arranged at that part but the elastic expansible/contractible property is not exhibited at that part. In FIG. 6, those elastic members other than the leg region elastic members are not shown.

According to the disposable diaper 1" of the fourth embodiment, the area E where the leg region elastic members 71 do not exhibit the elastic expansible/contractible property is formed at the part K where the absorbent core 4 exists, the same function and effect as the diapers of the first to third embodiments can be exhibited.

Moreover, since at least one portions of the extension parts 71a", 71b" located at the part where the absorbent core 4 exists exhibits the elastic expansible/contractible property, the opposite side parts of the absorbent core 4 are lifted upward and a concave pocket structure is formed at the under-crotch region C at the time of wearing the diaper in which a widthwise central area of the absorbent core 4 serves as a bottom part and the opposite side parts of the lifted absorbent core 4 serves as side wall parts. Thus, excellent anti-leakage property can be obtained. Moreover, since the extension parts 71a", 71b" are fixed at the part where the absorbent core exists by the second fixing means, the pocket structure is stabilized and excellent anti-leakage property can surely be obtained.

Since the girth region elastic members 9 are arranged at the girth region D, fitness around the wearer's girth part is enhanced, and wearing awareness and anti-leakage effect are by far improved. Moreover, since the girth region elastic members 9 do not exhibit the elastic expansible/contractible property at least at the widthwise central area of the part where the absorbent core 4 exists, the potential absorptive capability of the absorbent core can be exhibited to the maximum, and cost-down or the like can be achieved by miniaturization of the absorbent core and reduction of the material to be used. In addition, easy-to-wear and outer appearance can be improved extensively. Moreover, in the case where the disposable diaper 1" of the fourth embodiment is used as a disposable diaper for an adult person, an urine blotting pad (auxiliary absorbing instrument) can be separately inserted between the topsheet 2 and the wearer. In such a case, since shrinkage and twisting hardly occur to the absorbent core, the urine blotting pad can stably be placed in a predetermined position and therefore, leakage caused by displacement of the urine blotting pad can be prevented effectively.

A disposable diaper according to a fifth embodiment will now be described with reference to FIG. 7. The disposable diaper of this embodiment is different from the fourth embodiment only in the respect that the second fixing means is adhesive agent instead of heat sealing. Only those points different from the fourth embodiment will be mainly described and description on the same points same as the first embodiment is omitted.

In the disposable diaper of the fifth embodiment, as shown in FIG. 7, extension parts 71a", 71b" of first and second elastic members 71a, 71b and one parts of gather forming parts 71a', 71b' (nearby areas of the extension parts 71a", 71b") are fixed between two sheet materials which constitute an outer layer body 5 by adhesive agent as the second fixing means. The hatched parts S of FIG. 7 show the areas where adhesive agent as the second fixing means is applied. As shown in the illustration, one parts of the extension parts 71a", 71b" are fixed at the part where the absorbent core 4 exists by the second fixing means. In this embodiment, the generally entire areas S where the second means are applied are formed on the areas P1 where adhesive agent as the first fixing means is applied. Moreover, one portions of the extension parts 71a", 71b" located at the part K where the absorbent core 4 exists, i.e., portions J fixed by adhesive agent as the second fixing means in the respective extension parts, exhibit the elastic expansible/contractible property.

The fixing by adhesive agent as the second fixing means can be achieved by firmly adhering the two sheet materials which sandwichingly hold the elastic members and non-movably arresting the elastic members or adhering the elastic members to the sheet material(s) either on one or both sides.

The outer layer body 5 in the diaper of this embodiment can be manufactured in the same manner as the method for manufacturing the outer layer body 5 of the first embodiment only except that adhesive agent as the second fixing means is additionally applied to a predetermined part before sticking the other continuous sheet to the top of the continuous sheet 51A after the first and second elastic members 71a, 71b are introduced to the top of the continuous sheet 51A, and the fixing process by heat sealing after the cutting-off process is executed is eliminated.

Although several preferred embodiments of the present invention have been described hereinbefore, the present invention should not be construed as being limited to those embodiments but many changes can be made without departing from the gist of the present invention.

Figure 8A:
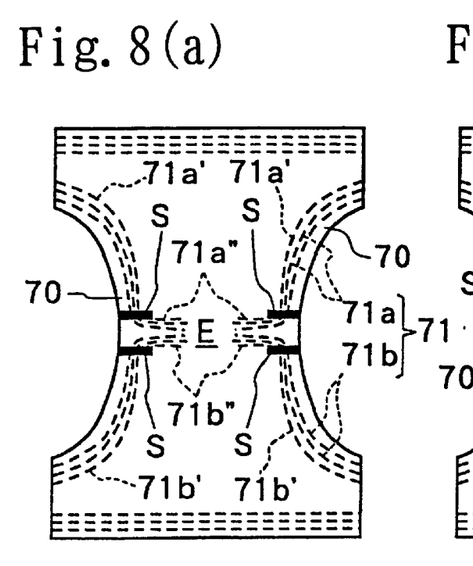
FIGS. 8(a) and 8(b) are schematic plan views showing a further embodiment of a disposable diaper according to the present invention, in which an absorptive main body is omitted and only an outer layer body is shown.
Figure 8B:
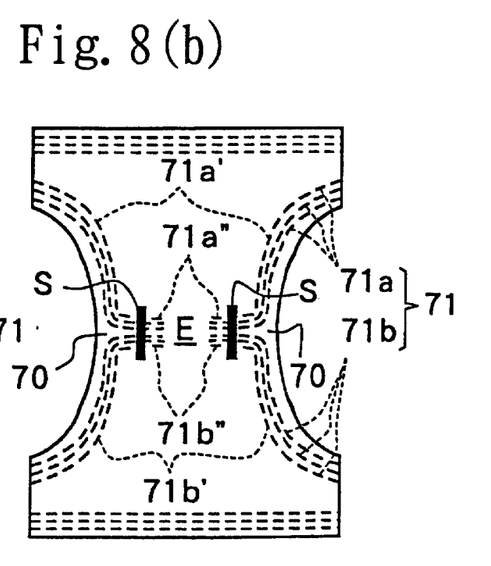

For example, the leg region elastic members may be arranged between the component sheet of the outer layer body 5 which does not form the outermost surface and the other sheet adjacent to the component sheet, or between the anti-leakage sheet 3 and the sheet constituting the outer layer body 5. Moreover, only selected one of the first and second elastic members 71a, 71b may be cut off. Moreover, only selected one of the first and second elastic members 71a, 71b may be fixed to a component of the diaper 1 by the second fixing means. Moreover, the oscillating pattern of the first and second elastic members 71a, 71b and the fixing part by the second fixing means may be the patterns and parts as shown in FIGS. 8(a) and 8(b). In FIGS. 8(a) and 8(b), the parts are indicated by S where heat sealing or adhesive agent as the second fixing means is applied. Each of the first and second elastic members 71a, 71b may be single or plural in number. Moreover, it is accepted that the first and/or second elastic members 71a, 71b do not exhibit the elastic expansible/contractible property at that part of the traversing parts 71a", 71b" where the absorbent core 4 exists. For example, at least one of the first and second elastic members may be cut off at plural places thereof into plural pieces so that the elastic expansible/contractible property is not exhibited. The girth region elastic member at the stomach-side region A and/or back-side region B may be eliminated. The fixing process in the third invention may be executed before or at the same time the cutting-off process is executed. The part K where the absorbent core exists can be not only a part where the first and second elastic members do not exist but also a part where the first and second elastic members exist but they do not exhibit the elastic expansible/contractible property there.

In the first and second inventions, the first fixing means can be a total fixing pattern instead of the intermittent fixing pattern as in the above-mentioned embodiments. Even if the first fixing means is a total fixing pattern, when the elastic body is cut off, its retaining force becomes insufficient and the rubber removal may occur. As a result, the leg region becomes unable to exhibit its expansible/contractible property. However, by employing the second fixing means, the rubber removal can be prevented from occurring at the leg region.

The first and/or second elastic member may be provided at the cut-off place with a shielding sheet for shielding the cut-off end part of the first and/or second elastic member. The end part formed by cut-off of the first and/or second elastic member is contracted and becomes unable to function. There is a possibility that the cut-off end is seen from outside and the outer layer sheet at the cut-off area is damaged to form a hole. By providing a shielding sheet at that part, a nice looking appearance can be obtained. In FIG. 2, the shielding sheet 53 is arranged at the internal side of the outer layer material 51 as indicated by imaginary lines. As the material for forming the shielding sheet 53, a high flexible sheet which can offer the feel resembling an underwear is preferable. Specifically, there can be listed, among others, a woven fabric, a nonwoven fabric, a film, a moisture-permeable film, an aperture film, a paper sheet and a composite material thereof. The expression "the first and second elastic members are arranged in such a manner as to traverse the absorbent core" does not necessarily require such an arrangement to be made before dividing, but it is good enough if there exists a will for making such an arrangement before dividing. Even if it occurs that an overlapped part between the absorbent core and the elastic members is not present by dividing (cut-off, in particular), it does not mean that this arrangement departs from the gist of the present invention. For example, even in the case where each elastic member is cut off between the gather forming parts and the opposite sides of the cut-off area are contracted to create a state in which no elastic member is located on the absorbent core, that portion which is arranged in such a manner as to traverse the absorbent core before cut-off can be called as the "traversing part".

The present invention can be applied not only to a shorts-type disposable diaper but also to a flat type disposable diaper having one pair of fastening tapes, a shorts-type sanitary napkin and the like.

According to an absorbent article of the first invention, since the elongation stress and the arrangement elongation rate of the elastic member for forming leg gathers can be established freely in order to obtain a proper tightening force around the wearer's leg at the time of production development, there can be obtained an absorbent article such as a disposable diaper capable of offering an improved nice fit and an improved absorptive capability, without accompanying with such inconveniences that flexibility around the wearer's leg is deteriorated, irritation the wearer's skin and the like.

According to an absorbent article of the second invention, there can be provided an absorbent article, in which the so-called "rubber removal" does not occur at the time of manufacture and wear, fitness and absorptive capability are enhanced, and a recess-shaped pocket structure is surely formed at the under-crotch region at the time of wear so that an excellent anti-leakage property can be obtained.

According to a method for manufacturing a laminated sheet of the third invention, there can easily and economically manufacture a laminated sheet which is suited to be used for manufacturing an absorbent article such as a disposable diaper and which is capable of easily obtaining a disposable diaper or the like in which fitness and absorptive capability are enhanced without accompanying with such inconveniences as deterioration of flexibility around the wearer's leg.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An absorbent article comprising a liquid-permeable topsheet, a liquid-impermeable anti-leakage sheet and a liquid-retentive absorbent core interposed between said topsheet and said anti-leakage sheet, a leg region elastic member for forming leg gathers being arranged in an elongated state thereof at a leg region arranged around a wearer's leg,
wherein said leg region elastic member comprises a first and a second elastic member, and said first and second elastic members each include a pair of gather forming parts arranged at a pair of said leg regions and a traversing part arranged in such a manner as to traverse said absorbent core, gather forming parts of said first and second elastic members at each leg region being arranged such that said gather forming parts are oriented in opposite directions with each other,
said gather forming parts of said first and second elastic members are fixed to a component of said absorbent article by a first fixing means, and
said first and/or second elastic members do not exhibit elastic expansible/contractible property at least at a widthwise central area of that part of said traversing part where said absorbent core exists, and a predetermined part of said first and/or second elastic member including a portion which does not exhibit elastic expansible/contractible property is fixed to the component of said absorbent article by a second fixing means.

2. An absorbent article according to claim 1, wherein said first and second elastic members do not exhibit their elastic expansible/contractible property at the part where said absorbent core exists.

3. An absorbent article according to claim 1, wherein said first fixing means is an adhesive agent and said second fixing means is a heat seal.

4. An absorbent article according to claim 1, wherein said first and second fixing means are adhesive agents.

5. An absorbent article according to claim 1, wherein said first and second elastic members are each cut off at said traversing part and fixed at opposite sides of the cut area in said traversing part by said second fixing means.

6. The absorbent article according to claim 1, further comprising an outer layer body, said anti-leakage sheet being joined to said outer layer body at a widthwise central area thereof, and wherein said first and second elastic members are located between said anti-leakage sheet and said outer layer body.

7. The absorbent article according to claim 1, further comprising a three-dimensional guard formed on each of left and right opposite side regions of the liquid-permeable top sheet, each of said three-dimensional guards including a plurality of elastic members fixed thereto for erecting said three-dimensional guards upwardly.

8. The absorbent article according to claim 1, wherein said gather forming parts of said first elastic member cross said gather forming parts of said second elastic member at each of said pair of leg regions to form a pair of crossing parts.

9. The absorbent article according to claim 1, wherein said first and second elastic members are each cut off at said traversing part to form said portion which does not exhibit elastic/contractible property to form a first portion where elastic members are provided but the elongated state of the elastic members is released, and a second portion where the elastic members do not exist.

10. A shorts-type absorbent article comprising a liquid-permeable topsheet, a liquid-impermeable anti-leakage sheet and a liquid-retentive absorbent core interposed between said topsheet and said anti-leakage sheet, a leg region elastic member for forming leg gathers arranged in an elongated state at a leg region arranged around a wearer's leg,
wherein said leg region elastic member comprises a first and a second elastic member, and said first and second elastic members each include a pair of gather forming parts arranged at a pair of said leg regions and an extension part extending from said gather forming parts towards a widthwise central area of said absorbent article,
said gather forming parts of said first and second elastic members are fixed to a component of said absorbent article by a first fixing means,
said extension part of said first and/or second elastic member is fixed to the component of said absorbent article by a second fixing means at a part where said absorbent core exists, and at least a portion of said extension part located at the part where said absorbent core exists exhibits elastic expansible/contractible property, and
said first and second elastic members do not exhibit elastic expansible/contractible property at least at a widthwise central area of the part where said absorbent core exists.

11. The absorbent article according to claim 10, further comprising an outer layer body, said anti-leakage sheet being joined to said outer layer body at a widthwise central area thereof, and wherein said first and second elastic members are located between said anti-leakage sheet and said outer layer body.

12. The absorbent according to claim 10, further comprising a three-dimensional guard formed on each of left and right opposite side regions of the liquid-permeable top sheet, each of said three-dimensional guards including a plurality of elastic members fixed thereto for erecting said three-dimensional guards upwardly.

13. The absorbent article according to claim 10, wherein said gather forming parts of said first elastic member cross said gather forming parts of said second elastic member at each of said pair of leg regions to form a pair of crossing parts.

14. The absorbent article according to claim 10, wherein said first and second elastic members are each cut off at said extension part to form said portion which does not exhibit elastic/contractible property to form a first portion where elastic members are provided but the elongated state of the elastic members is released, and a second portion where the elastic members do not exist.

15. A method for manufacturing a partly elasticized laminated sheet comprising the steps of applying an adhesive agent as first fixing means to at least one of two consecutive sheets which are stuck to each other in a predetermined pattern; sticking said two consecutive sheets together after said elastic member is introduced while oscillating said elastic member in a direction orthogonal to a flowing direction of said two consecutive sheets so that said elastic member is fixed between said two consecutive sheets through said adhesive agent; dividing said elastic member at a predetermined part; and fixing the predetermined part of said elastic member to at least one of said two consecutive sheets by second fixing means before or after, or at the same time said elastic member is divided.

* * * * *